United States Patent
Albrecht et al.

[11] 3,946,021
[45] Mar. 23, 1976

[54] BIS-BASIC KETONES OF CARBAZOLE

[75] Inventors: William L. Albrecht; Robert W. Fleming, both of Cincinnati, Ohio

[73] Assignee: Richardson-Merrell Inc., Wilton, Conn.

[22] Filed: June 28, 1973

[21] Appl. No.: 374,350

Related U.S. Application Data

[63] Continuation of Ser. No. 57,780, July 23, 1970, abandoned.

[52] U.S. Cl... 260/293.61; 260/246 B; 260/268 TR; 260/315; 424/248; 424/250; 424/267; 424/274
[51] Int. Cl.[2] .................................... C07D 295/12
[58] Field of Search..... 260/246 B, 268 TR, 293.61, 260/293.62, 315

[56] References Cited
UNITED STATES PATENTS

| | | | |
|---|---|---|---|
| 2,783,216 | 2/1957 | Martin | 260/63 |
| 2,840,558 | 6/1958 | Martin | 260/247.5 |
| 3,531,489 | 9/1970 | Albrecht et al. | 260/294.3 |
| 3,576,865 | 4/1971 | Fleming et al. | 260/559 |
| 3,592,819 | 7/1971 | Fleming et al. | 260/294.7 C |
| 3,647,860 | 3/1972 | Sill et al. | 260/475 FR |
| 3,673,191 | 6/1972 | Albrecht et al. | 260/293.57 |
| 3,707,471 | 12/1972 | Albrecht et al. | 260/293.62 |

*Primary Examiner*—G. Thomas Todd
*Attorney, Agent, or Firm*—George W. Rauchfuss, Jr.; Eugene O. Retter

[57] ABSTRACT

The novel bis-basic ketones of carbazole of the present invention have antiviral activity when administered orally and parenterally. These compounds are represented by the following formula:

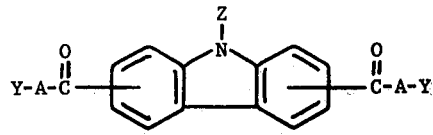

wherein Z is hydrogen or lower alkyl having from 1 to 4 carbon atoms; A is a straight or branched alkylene chain having from 1 to about 6 carbon atoms; and each Y is A. the group

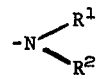

wherein $R^1$ and $R^2$ are individually hydrogen or lower alkyl having from 1 to about 4 carbon atoms; or B. the group

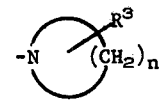

wherein $n$ is a whole integer of 4 or 5, and $R^3$ is hydrogen or lower alkyl having from 1 to about 4 carbon atoms and can be linked to any one of the carbon atoms of the heterocyclic group; or C. the group

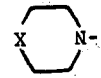

wherein X is oxygen or $NR^4$, and $R^4$ is hydrogen or lower alkyl of from 1 to about 4 carbon atoms; or a pharmaceutically acceptable acid addition salt of said base.

These new compounds can be prepared by several different methods which are described.

8 Claims, No Drawings

BIS-BASIC KETONES OF CARBAZOLE

This is a continuation of application Ser. No. 57,780 filed July 23, 1970, now abandoned.

This invention relates to novel bis-basic ketones of carbazole, their method of preparation and use as antiviral agents. The compounds of this invention include both the base form and pharmaceutically acceptable acid addition salts of the base wherein the base form is represented by the general formula

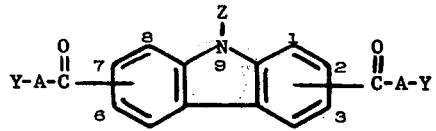

Formula I wherein Z is hydrogen or straight or branched lower alkyl having from 1 to 4 carbon atoms; each A is a straight or branched alkylene chain having from 1 to about 6 carbon atoms; and each Y is A. the group

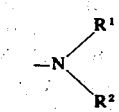

wherein $R^1$ and $R^2$ are individually hydrogen or lower alkyl having from 1 to about 4 carbon atoms; or B. the group

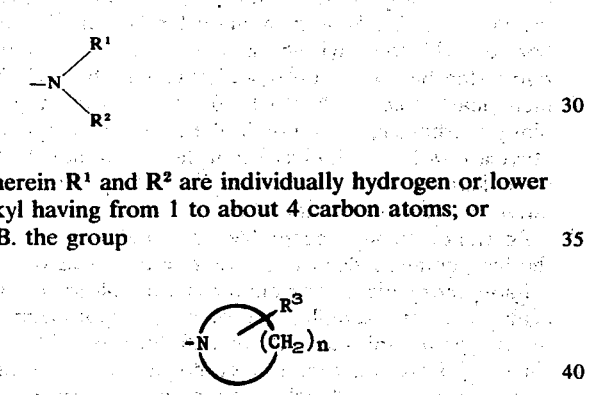

wherein n is a whole integer of 4 or 5, and $R^3$ is hydrogen or lower alkyl of from 1 to about 4 carbon atoms and can be linked to any one of the carbon atoms of the heterocyclic group; or C. the group

wherein X is oxygen or $NR^4$, and $R^4$ is hydrogen or lower alkyl of from 1 to about 4 carbon atoms.

As can be seen from the above Formula I, the basic ketone groups that is,

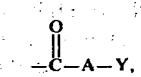

can be linked to the tricyclic ring system of carbazole by replacement of any of the four hydrogens of the benzenoid ring to which such group is attached. Thus, one of the groups can be in any of the positions 1 through 4 of the tricyclic ring system, and the other can be in any of the positions 5 through 8. Preferably one of the basic ketone groups is in the 3-position and the other is in the 6-position of the tricyclic ring system.

It is apparent from the above Formula I and its description that the compounds can have structures wherein Y is the group

as more fully shown by the following general Formula II, or wherein Y is the group

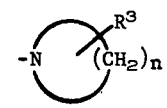

as more fully shown by the following general Formula III, or wherein Y is the group

as more fully shown by the following general Formula IV below:

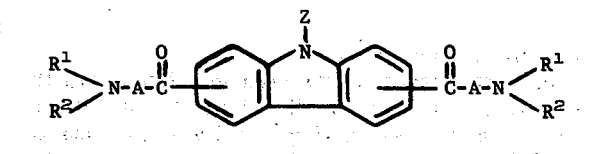

Formula II

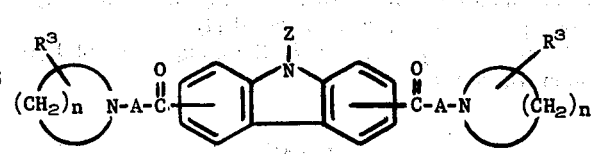

Formula III

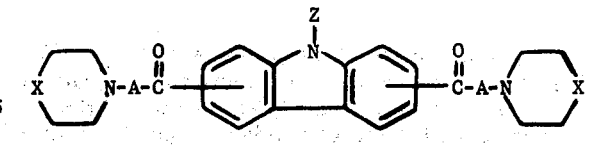

Formula IV

In the general Formulas II, III and IV the various symbols Z, A, $R^1$, $R^2$, $R^3$, X and n have the meanings defined hereinbefore.

In the compounds of the above Formulas I, II, III and IV, Z represents hydrogen or lower alkyl having from 1 to 4 carbon atoms. When Z represents lower alkyl having from 1 to 4 carbon atoms, such group may be attached to the tricyclic heterocyclic nitrogen atom through either the primary or secondary carbon atom of the lower alkyl group. Illustrative of lower alkyl groups as represented by Z there can be mentioned for example: methyl, ethyl, propyl, butyl and the like.

Each of the symbols A in the compounds of the above Formulas I, II, III and IV is an alkylene group having from 1 to about 6 carbon atoms which can be straight chain, that is, for example, $-CH_2-(CH_2)_m-$ wherein m is a whole integer from 0 to 5, or a branched chain. Each of the alkylene groups as represented by A can be the same or different. Preferably these groups are the same. Illustrative of alkylene groups as represented by A there can be mentioned for example: methylene, 1,2-ethylene, 1,3-propylene, 1,4-butylene, 1,5-pentylene, 1,6-hexylene, 2-methyl-1,4-butylene, 2-ethyl-1,4-butylene, 3-methyl-1,5-pentylene and the like.

Each amino group of the compounds of Formula II, that is,

can be a primary, a secondary or a tertiary amino group. Each $R^1$ and $R^2$ is individually hydrogen or lower alkyl having from 1 to about 4 carbon atoms. Preferably each of the amino groups as represented by

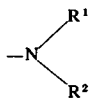

is a tertiary amino group.

The term lower alkyl as used in reference to the compounds of Formula II relates to straight or branched alkyl chains having from 1 to about 4 carbon atoms. Illustrative of lower alkyls as can be represented by each $R^1$ or $R^2$ in the compounds of Formula II there can be mentioned for example: methyl, ethyl, n-propyl, isopropyl, n-butyl and secondary-butyl.

Each heterocyclic group in the compounds of Formula III, that is

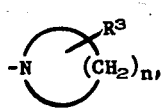

can be a 5- or 6-membered ring, that is, n is 4 or 5. The $R^3$ group can be hydrogen or a lower alkyl chain of from 1 to about 4 carbon atoms and can be attached to any one of the heterocyclic carbon atoms. Illustrative of heterocyclic groups as represented by each

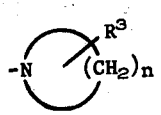

there can be mentioned for example: piperidino, pyrrolidino, 4-methylpiperidino, 3-methylpiperidino, 4-propylpiperidino and the like.

Each heterocyclic group of Formula IV, that is,

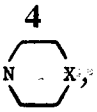

in addition to the one nitrogen atom, can contain a second hetero atom, that is, X is oxygen or $N-R^4$. The $R^4$ group can be hydrogen or a straight or branched lower alkyl chain of from 1 to about 4 carbon atoms. As examples of heterocyclic groups as represented by

there can be mentioned for example: morpholino, piperazino, N-(lower)alkylpiperazino, such as, for example N-methyl- or N-ethylpiperazino and the like.

Illustrative of base compounds of this invention as represented by Formula I there can be mentioned for example: N-ethyl-3,6-bis-(4-piperidinobutyryl)carbazole, N-ethyl-3,6-bis(4-dimethylaminobutyryl)carbazole, 3,6-bis(5-diethylaminovaleryl)-N-methylcarbazole, N-isopropyl-3,6-bis[4-(4-methylpiperidino)-butyryl]carbazole, 2,6-bis(4-diethylaminobutyryl)-N-methylcarbazole, N-ethyl-3,6-bis(3-pyrrolidinopropionyl)carbazole, 3,6-bis(2-diethylaminoacetyl)-N-ethylcarbazole, 3,6-bis(3-morpholinopropionyl)-N-methylcarbazole, 2,6-bis[4-(N-methylpiperazino)-butyryl]carbazole and the like.

Pharmaceutically acceptable acid addition salts of the base compounds of this invention are those of any suitable inorganic or organic acids. Suitable inorganic acids are, for example, hydrochloric, hydrobromic, sulfuric or phosphoric acids and the like. Suitable organic acids are, for example, carboxylic acids such as acetic, propionic, glycolic, lactic, pyruvic, malonic, succinic, fumaric, malic, tartaric, citric, ascorbic, maleic, hydroxymaleic, benzoic, hydroxybenzoic, phenylacetic, cinnamic, salicylic, 2-phenoxybenzoic and the like, or sulfonic acids such as methane sulfonic, 2-hydroxyethane sulfonic acid and the like. Mono- or di-acid salts may be formed, and the salts can be hydrated or substantially anhydrous.

The compounds of the present invention can be administered to animals such as warm-blooded animals and particularly mammals to prevent or inhibit infections of: picornaviruses, for example, encephalomyocarditis; myxo-viruses, for example, Influenza $A_2$ (Jap/305); arboviruses, for example, Semliki Forest; herpesvirus group, for example, herpes simplex; and poxviruses, for example Vaccinia IHD. When administered prior to infection, that is, prophylactically, it is preferred that the administration be within 0 to 96 hours prior to infection of the animal with pathogenic virus. When administered therapeutically to inhibit an infection, it is preferred that the administration be within about a day or two after infection with pathogenic virus.

The dosage administered will be dependent upon the virus for which treatment or prophylaxis is desired, the type of animal involved, its age, health, weight, extent of infection, kind of concurrent treatment, if any, frequency of treatment and the nature of the effect desired. Illustratively, dosage levels of the administered active ingredients can be: intravenous, 0.1 mg/kg; intraperitoneal, 0.1 to about 50 mg/kg; subcutaneous, 0.1 to about 250 mg/kg; oral, 0.1 to about 500 mg/kg and preferably about 1 to 250 mg/kg; intransal instillation, 0.1 to about 10 mg/kg; and aerosol, 0.1 to about 10 mg/kg of animal body weight.

The compounds may be administered, dissolved or suspended, in any conventional non-toxic pharmaceutical carrier of the type that may be taken orally, applied topically, buccally or parenterally.

One of the methods used to prepare the compounds of this invention is illustrated by the following reaction scheme:

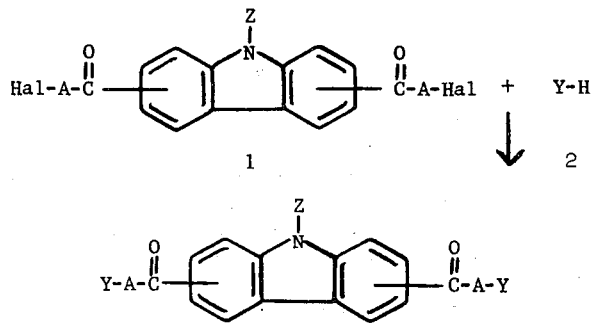

Formula I

In this reaction scheme Z, A and Y have the meaning defined hereinbefore, and each Hal is either chlorine, bromine or iodine.

The bis-(ω-haloalkanoyl)carbazole derivative, 1, in which the position of substitution is 3,6- can be prepared by a Friedel-Crafts acylation of carbazole. Of suitable acylating agents which may be used there can be mentioned for example: chloroacetyl chloride, bromoacetyl bromide, 3-chloropropionyl chloride, 4-chlorobutyryl chloride, 5-chlorovaleryl chloride, 5-chloro-4-methylvaleryl chloride, 5-chloro-3-methylvaleryl chloride and the like.

It is apparent that the acylation reaction may be carried out in a variety of solvents and under catalysis of a variety of Lewis acids. The temperature and duration of the reaction may be varied to allow for optimum reaction conditions. A preferred procedure is to combine one equivalent of carbazole with 2.5 equivalents of an acylating agent in methylene chloride followed by portionwise addition of aluminum chloride. The temperature of the reaction is maintained below zero degrees C with continuous stirring. After the additions are complete the temperature may be elevated to 25°–40°C for 12 to 36 hours. The reaction mixture is worked up in the usual manner by decomposing the complex with ice water/HCl. The product obtained is recrystallized from a suitable solvent, such as, methylene chloride, chloroform or the like. The procedure may be varied such that there is a reverse addition of acylating agent and Lewis acid, or a reverse addition of aromatic hydrocarbon and Lewis acid. The more reactive halogen derivative, that is, the bis(107-iodoalkanoyl)carbazole may be prepared from the corresponding bis-ω-chloro derivative using a halogen exchange reaction under the conditions generally employed in the Conant-Finkelstein reaction.

Of typical amines, 2, useful in the above reaction scheme there can be mentioned for example: ammonia, or a compound which is a potential source of ammonia such as, for example, hexamethylenetetramine and the like; primary amines such as ethylamine, propylamine and the like; and secondary amines such as diethylamine dibutylamine, piperidine, 4-methylpiperidine, morpholine, piperazine, N-ethylpiperazine and the like.

The amination of bis(ω-haloalkanoyl)carbazole, 1, may be carried out under a variety of conditions. For example, compound 1 may be heated together with a large excess of the amine, 2, the excess amine serving as the reaction medium and the hydrohalide acceptor. This method is particularly suitable for readily available amines, the excess of which can be easily removed from the reaction mixture by, for example, distillation at reduced pressure or by washing the product with water. Or, one equivalent of compound 1 and four equivalents of the amine, 2, may be heated together in one of a number of different types of solvents, for example, in aromatic solvents such as benzene, toluene, xylene, and the like; or ethers such as tetrahydrofuran, dioxane and the like; or ketones such as acetone, butanone and the like; or aprotic solvents such as N,N-dimethylformamide, N,N-dimethylacetamide, dimethyl sulfoxide and the like; or mixtures of these solvents with water. The reaction between compound 1, wherein the halogen is chlorine, and the amine, 2, is frequently promoted by the addition of either sodium or potassium iodide, the iodide being used in either catalytic or stoichiometric amounts. In some cases, it may be advantageous to use only two equivalents of the amine, 2, for each equivalent of the bis(ω-haloalkanoyl)carbazole, 1, an excess of an inorganic base such as powdered sodium or potassium carbonate being used as the hydrohalide acceptor. The reaction will proceed normally in 12 to 72 hours at temperatures of 20° to 150°C. When volatile amines are employed, the reaction is best carried out under pressure in a suitable pressure reactor or autoclave.

Alternatively, the amination reaction may be carried out on a derivative of compound 1 such as the bis-ketal carbazole derivative, which may be prepared by allowing bis(ω-haloalkanoyl)carbazole and an excess of ethyl orthoformate to react in the presence of an acid catalyst such as hydrochloric acid for several days in a polar solvent such as ethanol, tetrahydrofuran and the like.

The compounds of Formula I wherein A is an alkylene chain of 3 to 6 carbon atoms may also be prepared by the reaction of a Grignard reagent with a dinitrile of carbazole as represented by the following reaction scheme:

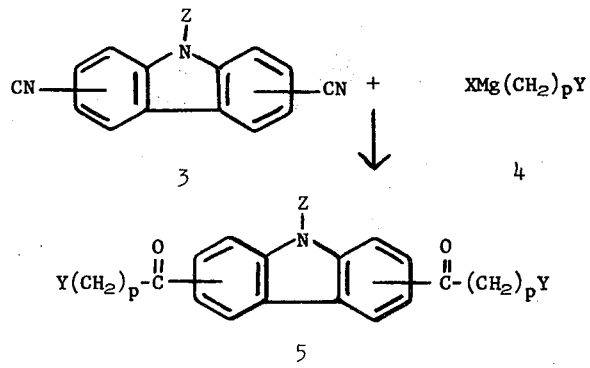

In the above reaction X is bromine or chlorine, p is 3 to 6, Z has the meaning defined hereinbefore, and Y may be any of the groups defined hereinbefore except those which contain a hydrogen attached to the nitrogen atom. When Z is hydrogen, an extra equivalent of the Grignard reagent, 4, must be added to the reaction mixture.

The reaction will proceed in from 1 to 24 hours at a temperature ranging from room temperature to about 80°C. The Grignard reagent, 4, may be prepared by reacting magnesium and an aminoalkyl halide of the formula

wherein X, $p$, and Y have the meaning defined hereinabove. The preferred solvent for this reaction is tetrahydrofuran.

The dicyanocarbazole derivative, 3, may be prepared from known carbazolediamines by a Sandmeyer reaction on the tetrazonium salts or from known carbazoledicarboxylic acids by dehydration of the corresponding amides by standard procedures.

Representative compounds of the present invention and several of the methods of preparing them, mentioned above, are illustrated in the following specific examples.

EXAMPLE 1

3,6-BIS(4-CHLOROBUTYRYL)-N-ETHYLCARBAZOLE

To a solution of 78.0g (0.4 mole) of N-ethylcarbazole and 141 g (1.0 mole) of 4-chlorobutyrylchloride in 1 l of methylene chloride, previously cooled to 0°C, 127.0 g (0.95 mole) of aluminum chloride was added portionwise. The mixture was stirred at room temperature for 16 hours, and the resulting complex was decomposed with concentrated HCl/ice. The organic layer was separated, washed with water, dried over magnesium sulfate and treated with pentane to precipitate the desired product which was recrystallized from acetone and then acetone-methanol. M.P. 106°–108°C, $\lambda_{max}^{EtOH}$ 259, $E_{1cm}^{1\%}$ 1030.

EXAMPLE 2

3,6-BIS(5-CHLOROVALERYL)-N-ETHYLCARBAZOLE

Following the procedure of Example 1 only substituting for 4-chlorobutyrylchloride the appropriate molar equivalent amount of 5-chlorovalerylchloride, the desired product was obtained. M.P. 94-95°C, $\lambda_{max}^{EtOH}$ 261, $E_{1cm}^{1\%}$ 974.

EXAMPLE 3

3,6-BIS(4-CHLOROBUTYRYL)CARBAZOLE

Following the procedure of Example 1, only substituting for N-ethylcarbazole, the appropriate molar equivalent amount of carbazole, the desired product was obtained and recrystallized from acetone-chloroform. M.P. 195–198°C.

EXAMPLE 4

3,6-BIS(5-CHLOROVALERYL)-N-METHYLCARBAZOLE

Following the procedure of Example 1, only substituting respectively for N-ethylcarbazole and 4-chlorobutyrylchloride, the appropriate molar equivalent amounts of N-methylcarbazole and 5-chlorovalerylchloride, the desired product is obtained.

EXAMPLE 5

3,6-BIS(4-CHLORO-2-METHYLBUTYRYL)-N-ETHYLCARBAZOLE

Following the procedure of Example 1, only substituting for 4-chlorobutyrylchloride the appropriate molar equivalent amount of 4-chloro-2-methylbutyrylchloride which is prepared by treating α-methyl-γ-butyrolactone with thionyl chloride and anhydrous zinc chloride [O. Wheeler and E. de Rodriquez, J. Org. Chem. 29, 1227(1964)] the desired product is obtained.

EXAMPLE 6

N-ETHYL-3,6-BIS(4-PIPERIDINOBUTYRYL)CARBAZOLE DIHYDROCHLORIDE HEMIHYDRATE

A mixture of 19.5 g (0.048 mole) of N-ethyl-3,6-bis(4-chlorobutyryl)carbazole, 34.0 g (0.4 mole) of piperidine and 2.0 g of potassium iodide in 250 ml of p-dioxane was heated at reflux for 68 hours with stirring, then filtered. Upon cooling the mixture was diluted with 500 ml of water, and the resulting semi-solid was dissolved in ether, washed repeatedly with water and dried over magnesium sulfate. The ethereal solution was treated with ethereal HCl to give the desired product which was recrystallized from methanol-ethyl acetate. M.P. 138°–142°C, $\lambda_{max}^{EtOH}$ 258, $E_{1cm}^{1\%}$ 699.

EXAMPLE 7

3,6-BIS(4-DIMETHYLAMINOBUTYRYL)-N-ETHYLCARBAZOLE BIS ACID FUMARATE

A mixture of 15.8 g (0.039 mole) of 3,6-bis(4-chlorobutyryl)-N-ethylcarbazole, 75 ml of 40% aqueous dimethylamine and 2 g of potassium iodide in 175 ml of p-dioxane was heated in a reaction bomb with stirring for 44 hours. The reaction mixture was concentrated to one-half its original volume in vacuo and diluted with 500 ml of water. The semi-solid which separated was dissolved in ether and washed repeatedly with water and dried over magnesium sulfate to give the free base which was treated with fumaric acid and recrystallized from butanone to give the desired product. M.P. 94°–98°C, $\lambda_{max}^{EtOH}$ 259, $E_{1cm}^{1\%}$ 611.

EXAMPLE 8

3,6-BIS(4-PIPERIDINOBUTYRYL)CARBAZOLE

A solution of 15.0 g (0.04 mole) of 3,6-bis(4-chlorobutyryl)carbazole, 85.0 g (1.0 mole) of piperidine and 2.0 g of potassium iodide in 15 ml of tetrahydrofuran was heated at 110°C in a reaction bomb for 24 hours with stirring. Upon cooling the reaction mixture was filtered and diluted with 700 ml of ice water. The resulting solid was washed with water, dried over magnesium sulfate and recrystallized from chloroformpetroleum ether (75°–90°C) and then from acetone to give the desired product. M.P. 171°–173°C, $\lambda_{max}^{EtOH}$ 259, $E_{1cm}^{1\%}$ 894.

EXAMPLE 9

3,6-BIS(5-DIETHYLAMINOVALERYL)-N-METHYLCARBAZOLE

Following the procedure of Example 7, only substituting respectively for 3,6-bis(4-chlorobutyryl)-N-ethylcarbazole and dimethylamine the appropriate molar equivalent amount of 3,6-bis(5-chlorovaleryl)-

N-methylcarbazole and an excess of diethylamine, the desired product is obtained.

EXAMPLE 10

2,6-BIS(4-DIETHYLAMINOBUTYRYL)-N-METHYLCARBAZOLE

To a solution of 2.5 equivalents of 3-diethylaminopropylmagnesium chloride and 3-diethylaminopropylchloride in tetrahydrofuran, is added dropwise a solution of 1-equivalent of 2,6-dicyano-N-methylcarbazole, which is prepared by converting 2,6-carbazoledicarboxamide to the corresponding N-methyl derivative by treatment with dimethylsulfate in the presence of sodium hydroxide and subsequently dehydrating the diamide by heating with phosphorous pentoxide, in tetrahydrofuran. When the addition is complete the reaction mixture is gently refluxed for 2 hours, then stirred at room temperature for several hours. The resulting complex is decomposed by treatment with saturated ammonium chloride, and the organic material is extracted with chloroform. The chloroform layer is treated with dilute HCl with warming. The aqueous solution is filtered, made alkaline and extracted with ether. The ether extract is dried over magnesium sulfate and evaporated to dryness to give the desired product.

EXAMPLE 11

3,6-BIS(4-AMINOBUTYRYL)CARBAZOLE DIHYDROCHLORIDE

An ethanolic solution of 1 equivalent of 3,6-bis(4-chlorobutyryl)carbazole and 2.4 equivalents of hexamethylenetetramine are reacted at reflux for 36 hours. The solution is acidified with 3N HCl, digested for several hours and the solvent removed under reduced pressure to give the desired product which is recrystallized from methanol-ethyl acetate.

EXAMPLE 12

3,6-BIS(4-ETHYLAMINOBUTYRYL)CARBAZOLE DIHYDROCHLORIDE

By the procedure of Example 11, only substituting for hexamethylenetetramine, a hundred fold excess of ethylamine, the desired product is obtained.

EXAMPLE 13

N-ETHYL-3,6-BIS(4-PIPERIDINO-2-METHYL-BUTYRYL)CARBAZOLE

Following the procedure of Example 6, only substituting for 3,6-bis(4-chlorobutyryl)-N-ethylcarbazole the appropriate molar equivalent amount of 3,6-bis(4-chloro-2-methylbutyryl)-N-ethylcarbazole, the desired product is obtained.

EXAMPLE 14

Following the procedure of Example 6, only substituting for piperidine the appropriate molar equivalent amounts of morpholine and N-methylpiperazine, the following compounds are prepared: N-Ethyl-3,6-bis(4-morpholinobutyryl)carbazole  N-Ethyl-3,6-bis[4-(N-methylpiperazino)butyryl]carbazole.

EXAMPLE 15

3,6-BIS(DIMETHYLAMINOACETYL)-N-ETHYLCARBAZOLE DIHYDROCHLORIDE DIHYDRATE

A mixture of 14.6 g (0.042 mole) of 3,6-bis(chloroacetyl)-N-ethylcarbazole, 100 ml of 40% dimethylamine and 7.0 g of potassium iodide in 200 ml of butanone is placed in a Paar bomb and heated at 70°–80°C with stirring for 2 hours. The reaction mixture is cooled and poured into 2.0 l of ice water. The solid which precipitates is filtered off, dissolved in chloroform and dried over magnesium sulfate to give the free base of the desired product which is subsequently converted to the dihydrochloride salt and recrystallized from methanol-acetone to give the desired product.

EXAMPLE 16

Following the procedure of Example 15, only substituting for dimethylaminie an excess amount of diethylamine and piperidine, the following compounds are prepared.
N-Ethyl-3,6-bis(diethylaminoacetyl)carbazole dihydrochloride
N-Ethyl-3,6-bis(piperidinoacetyl)carbazole dihydrochloride.

What is claimed is:

1. A compound selected from a base of the formula

wherein Z is a member selected from the group consisting of hydrogen or lower alkyl having from 1 to 4 carbon atoms; each A is a straight or branched alkylene chain having from 1 to 6 carbon atoms; and each Y is a member selected from the group consisting of A. the group

wherein $R^1$ and $R^2$ are individually selected from the group consisting of hydrogen or lower alkyl having from 1 to 4 carbon atoms; of B. the group

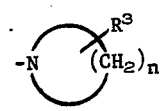

wherein $n$ is a whole integer of 4 or 5, and $R^3$ is selected from the group consisting of hydrogen or lower alkyl having from 1 to 4 carbon atoms and can be linked to any one of the carbon atoms of the heterocyclic group; or C. the group

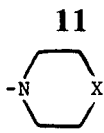

wherein X is oxygen or NR⁴, and R⁴ is selected from the group consisting of hydrogen or lower alkyl of from 1 to 4 carbon atoms; or a pharmaceutically acceptable acid addition salt of said base.

2. A compound of claim 1 wherein each Y is the group

and one of said

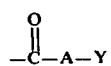

groups is in the 2- or 3-position of the carbazole ring and the remaining

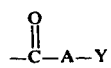

group is in the 6-position of the carbazole ring.

3. A compound of claim 1 wherein each Y is the group

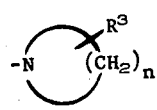

and one of said

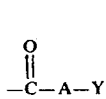

groups is in the 2- or 3-position of the carbazole ring and the remaining

group is in the 6-position of the carbazole ring.

4. A compound of claim 3 wherein n is the integer 5.

5. A compound of claim 1 wherein each Y is the group

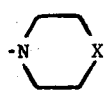

and one of said

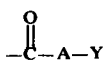

groups is in the 2- or 3-position of the carbazole ring and the remaining

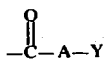

group is in the 6-position of the carbazole ring.

6. A compound of claim 1 which is N-ethyl-3,6-bis(4-piperidinobutyryl)carbazole or a pharmaceutically acceptable acid addition salt of said base.

7. A compound of claim 1 which is 3,6-bis[4-(dimethylamino)butyryl]-N-ethylcarbazole or a pharmaceutically acceptable acid addition salt of said base.

8. A compound of claim 1 which is 3,6-bis(4-piperidinobutyryl)carbazole or a pharmaceutically acceptable acid addition salt of said base.

* * * * *

UNITED STATES PATENT AND TRADEMARK OFFICE
CERTIFICATE OF CORRECTION

PATENT NO. : 3,946,021
DATED : March 23, 1976
INVENTOR(S) : William L. Albrecht and Robert W. Fleming It is certified that error appears in the above-identified patent and that said Letters Patent are hereby corrected as shown below:

Column 4, lines 25-26 -- "N-ethyl-3,6-bis(4-piperidino-butyryl)carbazole, N-ethyl-3,6-bis(4-dimethylaminobutyryl)-carbazole," should read "N-ethyl-3,6-bis(4-piperidino-butyryl)carbazole, 3,6-bis(4-piperidinobutyryl)carbazole, N-ethyl-3,6-bis(4-dimethylaminobutyryl)carbazole,".
Column 5, line 61, "bis(107-iodoalkanoyl)" should read "bis($\omega$-iodoalkanoyl)".

Signed and Sealed this

Twenty-second Day of November 1977

[SEAL]

Attest:

RUTH C. MASON
Attesting Officer

LUTRELLE F. PARKER
Acting Commissioner of Patents and Trademarks